United States Patent
Gomez et al.

(10) Patent No.: US 10,660,508 B1
(45) Date of Patent: May 26, 2020

(54) NEEDLESCOPIC INSTRUMENT SYSTEM

(71) Applicant: Innerspace Surgical Corporation, Pompano Beach, FL (US)

(72) Inventors: Ricardo Alexander Gomez, Lighthouse, FL (US); Sandy Lawrence Heck, Los Angeles, CA (US); Eric William Conley, South Berwick, ME (US)

(73) Assignee: INNERSPACE SURGICAL CORPORATION, Pompano Beach, FL (US)

( * ) Notice: Subject to any disclaimer, the term of this patent is extended or adjusted under 35 U.S.C. 154(b) by 1052 days.

(21) Appl. No.: 14/849,833

(22) Filed: Sep. 10, 2015

Related U.S. Application Data

(60) Provisional application No. 62/048,566, filed on Sep. 10, 2014.

(51) Int. Cl.
*A61B 1/00* (2006.01)
*A61B 1/313* (2006.01)
*A61B 17/34* (2006.01)

(52) U.S. Cl.
CPC ...... *A61B 1/00128* (2013.01); *A61B 1/00101* (2013.01); *A61B 1/3132* (2013.01); *A61B 17/3478* (2013.01)

(58) Field of Classification Search
CPC .............. A61B 1/00101; A61B 1/3132; A61B 17/3478; A61B 1/00128; A61B 1/00087
See application file for complete search history.

(56) References Cited

U.S. PATENT DOCUMENTS

| | | | | |
|---|---|---|---|---|
| 5,441,059 | A * | 8/1995 | Dannan | A61B 17/00234 128/898 |
| 2011/0087266 | A1* | 4/2011 | Conlon | A61B 17/29 606/205 |
| 2012/0083778 | A1* | 4/2012 | McGaffigan | A61B 18/085 606/28 |
| 2012/0289773 | A1* | 11/2012 | Joshi | A61B 17/29 600/104 |
| 2014/0074135 | A1* | 3/2014 | Hart | A61B 1/00087 606/170 |

\* cited by examiner

*Primary Examiner* — Matthew F Desanto
(74) *Attorney, Agent, or Firm* — Grogan, Tuccillo & Vanderleeden, LLP

(57) ABSTRACT

The present invention relates to devices and methods for use in minimally invasive procedures whereby at least one, and preferably a plurality of laparoscopic instrument heads can be delivered through a single trocar and made accessible for attachment within a body cavity to the distal end of a needlescopic instrument under direct visualization via a laparoscope. The system and procedure will produce less scarring, less pain, and a reduced risk of infection at the surgical site. An addition benefit is that, because only 1 trocar is used instead of 3-5 trocars, there is a significant cost saving in each case and the surgeon is freer to move instrument locations and add/remove instruments since a new trocar does not need to be inserted every time.

16 Claims, 8 Drawing Sheets

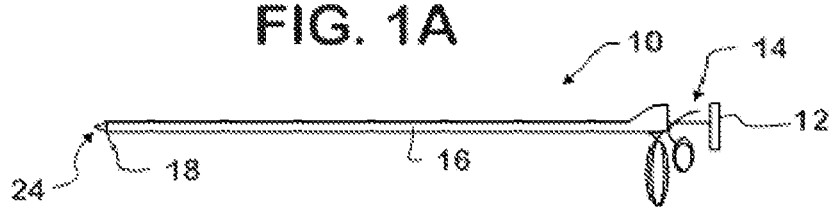
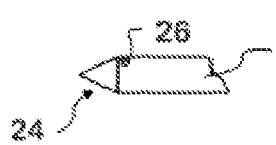
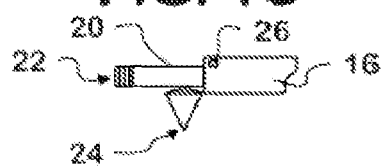
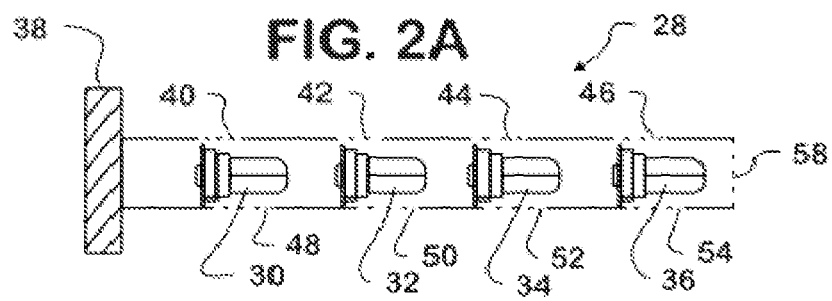
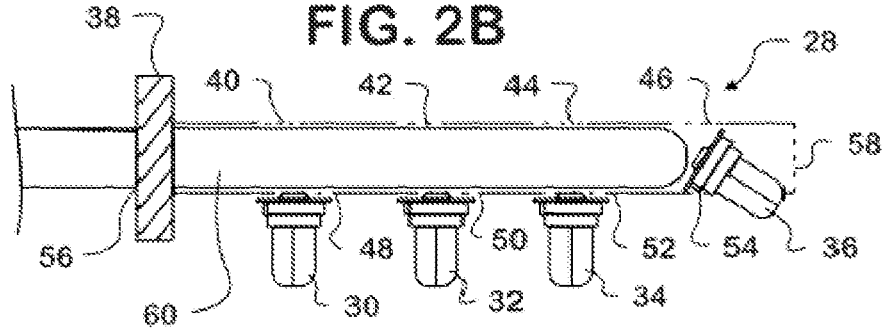

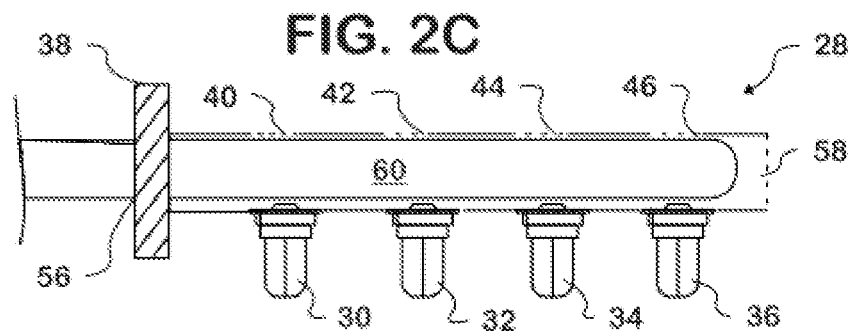
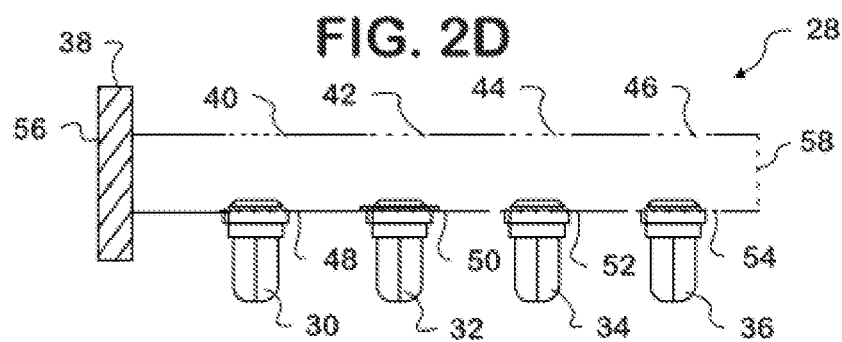
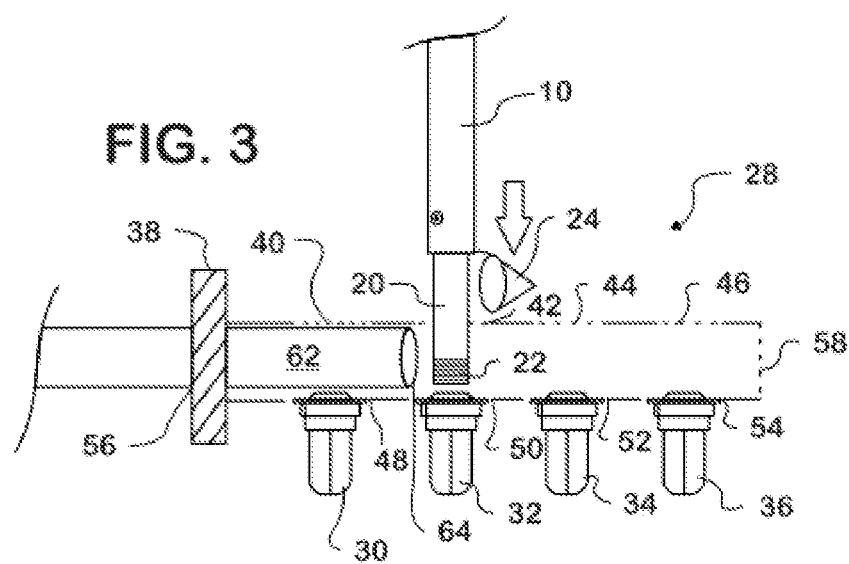

NEEDLESCOPIC INSTRUMENT SYSTEM

CROSS REFERENCE TO RELATED APPLICATIONS

This application claims priority from U.S. Provisional Application No. 62/048,566 filed on Sep. 10, 2014, having the identical title and is incorporated by reference as if fully restated herein.

FIELD OF INVENTION

The present invention is directed toward systems and methods for attaching any desired one of a plurality of interchangeable laparoscopy heads at any given time to a needlescopic instrument, while both the heads and needlescopic instrument are positioned within a body cavity. The methods and systems exemplified herein do not preclude their use with a single laparoscopic head if so desired.

BACKGROUND OF INVENTION

Laparoscopy is a surgical procedure performed through small incisions in the abdomen using specialized instruments. A thin cylindrical instrument called a laparoscope, connected to a camera, is used to provide a clear picture of the abdominal cavity to the surgeon.

Prior to starting a surgical procedure a small incision is created, and then a trocar is inserted through the incision. Trocars typically range in diameter from 5 to 12 mm and provide a passageway for the introduction of medical devices into the abdomen. Typically, several incisions 5-12 mm in length are created. An insufflator is also used to inflate the cavity with carbon dioxide, thus creating space for the surgeon to perform the medical procedure and providing a viewing field. A special medical device called a laparoscope is inserted through the trocar so the surgeon can view the cavity content.

The origins of the word laparoscope can be traced back to the Greek word for "laparo" meaning "flank," which is the area of the body located between the ribs and hips, commonly referred to as the abdomen, and the word "scope" which means to look at or examine. Hence laparoscopes provide means for viewing the interior of the abdomen of a patient.

The first use of a laparoscope goes as far back as 400 BC where the physician Hippocrates (460-377 BC) mentioned the use of a device called a rectoscope. Its use was for inspecting the oral cavity and pharynx of a person. When a tool is used to view the interior of a person through a natural opening in the body, such as through the mouth or nose, it is more accurately referred to as an endoscope. Laparoscopes and endoscopes have allowed for tremendous strides forward in the medical field.

It wasn't until 1805 that a physician named Phillip Bozzini of Mainz, Germany invented the lichtleiter, also referred to as the Bozzini Endoscope. The lichtleiter consisted of two parts: (1) a light container with an optical part and (2) a mechanical part which consisted of viewing tubes adapted to fit inside a body cavity. The lichtleiter was a tube incorporating various attachments which used concave lenses, with half of the tube transmitting light from a candle to the tip of the device and the other half returning the reflected light, providing the surgeon an interior view of a cavity. Thus, the candle, with angled mirrors inside the device, provides the light that enables the physician to see into the abdominal cavity. This approach was not practical because of its limitations of maintaining a heated light source, but it was the predecessor of today's laparoscopes and, at the time, was the first device to allow inspection of the interior of a body cavity.

In 1901, George Kelling performed a laparoscopy on a dog using a technique that introduced air into the abdominal cavity. In 1910 Victor Elner used a gastroscope to view the inside of a stomach and shortly thereafter a flexible gastroscope was designed. Thereafter, in 1911, the first laparoscopy was performed on a human by the Swedish doctor H. C. Jacobeus. In spite of the technical advances that were being made, problems persisted, such as the heat produced at the distal tip of the scope and visualization troubles, such as blind spots being present in the field of view, all limiting the use of laparoscopes. Its main purpose thus remained for diagnostic purposes.

In the early 20th century, with the invention of the light bulb and electrical devices by Thomas Edison, significant advances began taking place; finally small light sources could be attached to the distal tip of laparoscopes without the need for cooling. The next great evolution took place in the 1950's when significant advances in fiber optics provided greater flexibility and the introduction of small light sources at the distal tip of the laparoscope into the abdomen without burning the patient's tissues.

As the art of surgery kept evolving, limited interest was focused on minimally invasive type surgeries. However, as some of the many advantages became apparent, such as lower operating cost, less patient trauma, less scarring, less pain, fewer surgical complications, quicker recovery times, shortened hospital stays, and less chance of infection, a need developed to find therapeutic uses for laparoscopes. In the 1970's, thanks to gynecologists and gastroenterologists, the use of laparoscopy began changing from diagnostic to therapeutic.

The development of miniaturized high-resolution television cameras and CCDs (charged coupled devices) propelled advances in therapeutic use of laparoscopes. As problems presented themselves, inventors focused on solutions that kept laparoscopy moving forward. An example of how a problem in laparoscopy led to a solution is the problem of lens fogging during visualization which developed in surgery due to intermittent insertion and removal of a laparoscope from within a body cavity. Inventors, such as Ricardo Alexander Gomez and Sandy Lawrence Heck developed and patented a revolutionary method for maintaining laparoscopic lenses crystal clear during procedures and dramatically improved the visualization and effectiveness of these types of surgeries with the use of a device called a D-Help®. Today there is a need for smaller and more effective laparoscopic tools, means of providing direct visualization and methods that minimize the use of additional trocars inserted into a patient's abdominal cavity.

As the field of minimally invasive surgery continues evolving, less invasive techniques are desired and the need for smaller laparoscopic tools also developed. A newer version of laparoscopy has developed and is referred to as needlescopic surgery. Needlescopic surgery is an advance over laparoscopic surgery inasmuch as incisions smaller than 3 millimeters are now possible. Virtually no scarring occurs, pain is reduced, and recovery times are faster. The problem associated with this new procedure is the limited functionality of the insertion instrument. As these instruments became thinner, the heads of the instruments also became smaller and were too small to effectively manipulate tissues and organs. For this reason, among others, needlescopic surgery is not functional for most procedures and has not been adopted by the surgical community.

People have experimented with the concept of attaching larger instrument heads to thin shafts inside the body, but no effective method has been developed to facilitate the insertion and attachment of such instrument heads within the body.

It has been a long term goal of surgeons specializing in minimally invasive procedures to be able to perform surgery with much smaller incisions while still having means to view the area of interest within the cavity. Therefore, there is a need in the field of needlescopic surgery for means for effectively providing and attaching laparoscopic sized instrument heads to small diameter instrument shafts such as needlescopic shafts within the body cavity while using direct visualization such that the number and size of the incisions are minimized.

These objectives being met, as well as other aspects, features and advantages of the present invention will become more readily apparent from perusal of the figures and detailed description of exemplary preferred embodiments, which follow.

SUMMARY OF INVENTION

The present invention is directed toward devices and methods for use in minimally invasive needlescopic procedures whereby one or more larger sized laparoscopic instrument heads can be delivered through a single trocar and made accessible for attachment within the body to the distal end of a small diameter needlescopic instrument shaft. The present invention is intended to reduce incision sizes and to reduce the number of trocars required, while still providing laparoscope sized instrument heads, still allowing for the use of standard laparoscopes, and allowing for attachment and detachment of various laparoscopic heads to a needlescopic instrument under direct visualization within a body cavity.

In one embodiment, the delivery of laparoscopic heads into the body is achieved through use of a hollow sleeve inserted into a trocar, the sleeve having symmetrically positioned perforated openings therein and preconfigured laparoscopic heads positioned within the lumen of the sleeve, for use with a laparoscope for direct visualization. Through use of a plunger, a spring actuated hinge, or other suitable mechanism, the laparoscopic heads may be moved out of the lumen of the sleeve and properly positioned within the body cavity for engagement to a needlescopic instrument. These heads may be held in position by fitted holders, magnets, or in any other suitable fashion which would hold them in place as they are pushed out of the lumen of the sleeve without falling into the body cavity. The sleeve would further allow passage of a laparoscope, while maintaining the heads in position for attachment to the distal end of a needlescopic instrument inserted at a desired location elsewhere through the abdominal wall. The symmetrical openings provide sufficient access for a needlescopic instrument shaft to be inserted therethrough and to be properly attached to and detached from a desired head, one at a time. Since the hollow sleeve permits the passage of a laparoscope therethrough while positioning the heads at a favorable laparoscopic viewing angle, direct visualization is maintained throughout the entire engagement process and there is no need for additional trocar/cannula incisions. Other versions of this exemplary embodiment may have an entirely open longitudinal peripheral area along the sleeve, in the fashion of a canoe, with the longitudinal opening being positioned opposite from where the heads are positioned. Further versions of this embodiment may also have the heads pushed out of the sleeve in a radial fashion, or in series along the length of the sleeve, or in any other suitable pattern which may be devised.

According to another exemplary embodiment, there is provided a needlescopic instrument capable of being inserted through the abdominal wall without need of a trocar, although small trocars could be used if desired, and then being attached distally to a laparoscopic head, a plurality of which have already been inserted into the body cavity through a trocar. The needlescopic instrument shaft comprises an elongated hollow shaft attached to control handles, or grips, at its proximal end, which provide the functions of opening, closing, rotating, extending, retracting, and holding the instrument head in position after being suitably engaged to the shaft The needlescopic instrument may include an inner movable rod along its longitudinal axis that extends from the proximal end at which is attached to a handle, to a pointed distal end designed to pierce the abdominal wall and then engage the laparoscopic head. The distal end may also include any suitable tapered/pointed end locking means such a pressure fit, magnets, clips, locks, hinges or loops for securing a laparoscopic head to the needlescopic instrument shaft. The invention is not limited to these configurations but may employ various different attachment configurations for securing the laparoscopic head to the control means.

In a further embodiment a needlescopic device having a hollow elongated shaft along its longitudinal axis is used. The hollow shaft contains an inner movable rod extending from the proximal end, to the distal end of the shaft. At the proximal end the movable rod is attached to an instrument control handle which transfers the movements to the threaded distal end. The distal end of the shaft incorporates a mating mechanism that allows the shaft tip to screw or click into the laparoscopic head. The distal shaft preferably comprises a sharp tip assembly which is shaped to reversibly clip into an opening in the laparoscopic head. Alternatively, a screw feature or a latching feature can be incorporated into the distal shaft. The sharp point facilitates entering through the abdominal wall, and then directly engages the laparoscopic head or opens to expose an inner locking/engagement mechanism. The locking mechanism may comprise mechanical means such as a metal clip, threaded device, a latching mechanism or any of the other suitable embodiments as used in the industry as a standard means of attachment. Multiple connections may be required, including connections to both the inner and outer shafts, and a combination of different mating mechanisms may be used within a single instrument.

In another embodiment, a laparoscopic head carrying device or rack containing at least one head is inserted into a trocar/cannula. The one or more heads are prepositioned inside a hollow elongated passageway along the device, minimizing the width and length of the device. A push rod is preferably used to deploy the instrument head(s) to a fully deployed position where it is then locked/held in place by mechanical or other suitable means, and is in the proper orientation for direct visualization through a laparascope inserted therein to make sure the head is properly secured to the needlescopic instrument. The device when fully deployed will be understood to allow other instruments to pass freely through its hollow passageway.

The laparoscope is then inserted into the trocar and is used to maintain direct visualization during the entire attachment/detachment process. The needlescopic instrument is then properly secured the laparoscopic head by mechanical means. The mechanical means are not limited to but includes being screwed, latched, clipped, joined, fastened, or locked in place. Proper attachment is assured by direct visualization with the laparoscope. There are no such embodiments in the field that maintain direct visualization of the attachment of the laparoscopic head to a distal end of a needlescopic instrument within the abdomen of a patient without requiring creation of a secondary trocar/cannula opening.

Several of the benefits of direct visualization are: quicker head placement, shorter surgery times, less invasive openings, and means of visually assuring the engagement of the laparoscopic head to the needlescopic instrument. When it comes time to replace the head, the head is reinserted through the corresponding access port in the rack, or otherwise brought back to the where it was "held" in the rack, locked/secured into position, and then unscrewed/unlatched (depending on the method used for attachment) from the needlescopic instrument. The needlescopic is then attached to another desired head and the procedure is repeated. Additional needlescopic instruments can be inserted through the abdominal wall as needed and wherever needed, and can provide additional benefits to the surgeon; the surgeon can now insert multiple instruments, and change their positions much more freely than is possible in standard laparoscopy, since the cost (in terms of money, scarring, post-op pain, and surgical site infection risk) is minimized due to the fact that trocars are not needed and the incisions are small.

In another embodiment an illustration of the abdomen is shown whereby the needlescopic device and laparoscope are shown as used during direct visualization. No other trocar/cannula openings are needed to perform surgical procedures.

Several of the advantages of providing direct visualization in the attachment and detachment of needlescopic devices from functional heads are: quicker tool exchanges, shorter procedure times, no additional trocars/cannulas and confirmation of engagement. Specifically, the invention provides means of direct visualization while attachment and detachment of the heads positioned within the body cavity takes place. The invention employs a rack device that once inserted through a standard trocar permits the interchangeable heads to be deployed. The invention may include a shorter trocar/cannula whereby the rack extends beyond a distal end of the trocar/cannula to expose the rack within the abdomen. The invention may also include a specialized trocar that incorporates the rack capable of holding and presenting the heads.

In another embodiment, the instrument heads are inserted through the trocar, and clipped/attached onto the outer edge of the distal trocar, thereby holding them in place along the periphery of the distal edge of the trocar. Such configuration which could allow insertion of the heads one at a time or all at once, would not require a hollow sleeve, but would have the heads attached via wires or other materials running along the inner or outer surface of the trocar to a proximal control mechanism that could be controlled outside of the body to move the heads forward into position for engagement along the distal shaft. Because the heads are held to the outer surface of the trocar/cannula, they would not impede passage of the laparoscope or other tools through the single trocar. In another embodiment, the heads are held along the distal edge of the trocar radially at a 90 degree angle from the trocar edge or any angle that best facilitates visualization.

There is a need in the field for a functional system that allows a user to maintain direct visualization while attaching laparoscopic heads positioned within the body to the distal end of a needlescopic instrument. These and other aspects, features and advantages of the present invention will become more readily apparent from the attached drawings and the detailed description of the preferred embodiments which follow.

BRIEF DESCRIPTION OF DRAWINGS

The preferred embodiments of the invention will hereinafter be described in conjunction with the appended drawings provided to illustrate and not to limit the invention, in which:

FIG. 1A provides a longitudinal perspective view of an exemplary embodiment of a needlescopic instrument;

FIG. 1B provides an enlarged perspective view of a distal tip of the needlescopic instrument with the tip cover assembly closed in position for piercing into a body cavity;

FIG. 1C provides an enlarged perspective view of the distal tip of the needlescopic instrument with the tip cover assembly open and a sliding threaded rod thereof shown deployed past the distal tip into position for engaging a functional head;

FIG. 2A provides a longitudinal sectional view of an exemplary head rack system made in accordance with the teachings of the present invention and shows the system with interchanageable laparascopic heads in a position maintained while being inserted into a body cavity;

FIG. 2B provides a longitudinal sectional view of the system of FIG. 2A showing the instrument heads being pivoted into their proper positions for potential engagement to the sliding threaded rod of the needlescopic instrument by a plunger;

FIG. 2C provides a longitudinal sectional view showing the plunger fully inserted into the rack with the interchangeable heads in proper position for engagement to the threaded rod of the needlescopic instrument;

FIG. 2D provides a sectional view of the rack with instrument heads properly positioned and the plunger having been withdrawn;

FIG. 3 provides a longitudinal sectional view through the system with a desired one of the plurality of available heads being directly visualized via a laparoscope prior to attachment thereof to distal end of threaded rod extending outwardly of distal end of the needlescopic instrument;

Like reference numerals refer to like parts throughout the several views of the drawings.

DETAILED DESCRIPTION

Figure 4:
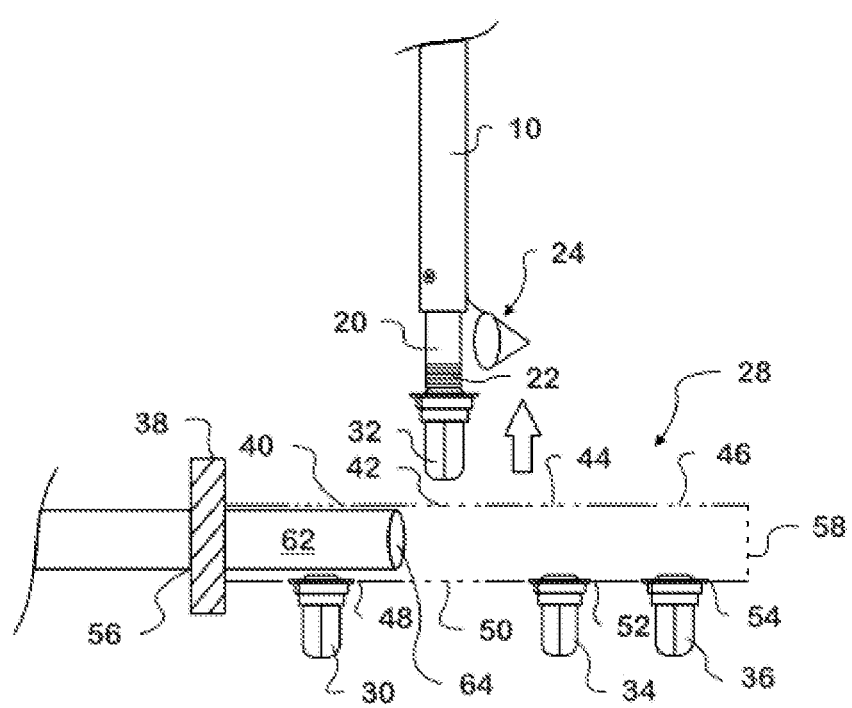
FIG. 4 provides a longitudinal sectional view similar to FIG. 4 but now showing one instrument head fully attached to the thread end of the needlescopic instrument and being removed from within the rack.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise With respect to FIG. 1A, a needlescopic instrument or needlescopic instrument (10) is illustrated having an instrument control handle (12) at the proximal end (14), a hollow shaft (16) that extends from the proximal end (14) to the distal end (18). The hollow shaft (16) houses a sliding threaded rod (20) controlled by the instrument control handle (12) that freely slides through the hollow shaft (16) when the instrument control handle (12) is engaged. The sliding rod (20) has a threaded end (22) that is housed in the distal end (18) of the needlescopic instrument (10). Attached to the distal end (18) of the needlescopic instrument (10) is a tip cover assembly (24). The forward movement of the sliding rod (20) by control handle (12) actuates the opening of the tip cover assembly (24). The tip cover assembly (24) is preferably hingedly engaged to the hollow shaft (16) by a locking mechanism (26) (FIGS. 1B and 1C) secures the closed position of the tip cover assembly (24).

In FIG. 1B, the instrument control handle (12) has not been engaged and the tip cover assembly (24) is in the closed position while in FIG. 1C the instrument control handle (12) has been engaged, causing the sliding threaded rod (20) to extend forwardly, opening the locking mechanism (26) and the tip cover assembly (24) from closed to open, allowing the threaded end (22) of the sliding rod (20) to extend past the distal end (18) of the needlescopic instrument (10).

Turning now to FIG. 2A, a rack or carrying device (28) for laparoscopic heads is illustrated showing the heads (30, 32, 34, and 36) generically in their delivery position to pass through the trocar/cannula device (38). Several cooperating upper needlescopic instrument access ports (40, 42, 44, 46) and cooperating lower instrument head deployment positioning ports (48, 50, 52, 54) corresponding to the instrument heads (30, 32, 34, and 36, respectively) are shown. A proximal opening (56) (FIG. 2B) and a distal opening (58) of the head rack or carrying device (28) allows a plunger (60) to be inserted into and completely through the rack (28) and pivot the heads (30, 32, 34, 36) into their proper positions in the lower instrument head position ports (48, 50, 52, 54) for attachment to the threaded end (22) of the needlescopic instrument (10) inserted through corresponding cooperating needlescopic instrument access ports (40, 42, 44, 46). Carrying devices that hold a single head (not shown) may be preferable in situations where only one head is needed, or the desired head is long.

Turning now to FIG. 2B the plunger (60) is used to pivot the instrument heads (30, 32, 34, 36) into the lower instrument head position ports (48, 50, 52, 54) for attachment to the threaded end (22) of the needlescopic instrument (10) via the corresponding cooperating needlescopic instrument access ports (40, 42, 44, 46).

Turning now to FIG. 2C, all the instrument heads (30, 32, 34, 36) have been pivoted into the lower instrument head position ports (48, 50, 52, 54) and are ready to be attached to the threaded end (22) of needlescopic instrument (10) via the upper access sports (40, 42, 44, 46). The lower instrument head position ports (48, 50, 52, and 54) are vertically aligned with the cooperating upper access ports (40, 42, 44, and 46).

Turning now to FIG. 2D, the instrument heads (30, 32, 34, 36) are deployed into the lower instrument head position ports (48, 50, 52, 54) and the plunger (60) has been removed from within the head rack (28).

Turning now to FIG. 3, the instrument control handle (12) (FIG. 1) of the needlescopic instrument (10) has been engaged and the sliding threaded rod (20) has opened tip cover assembly (24). The threaded end (22) is passed through a desired one of the upper access ports to engage a desired laparoscopic head. A laparoscope (62) is inserted through the trocar/cannula device (38) and into the proximal opening (56) into the instrument rack (28), and provides direct visualization of the attachment and detachment process of the threaded end (22) to any desired one of the instrument heads (30, 32, 34, 36). The distal lens (64) of the laparoscope (62) transmits the view electronically back through a monitor connector (not shown) for viewing Turning now to FIG. 4, the tip cover assembly (24) is in the open position and the threaded end (22) of the sliding threaded rod (20) is shown removing an instrument head (32) from its position port (50), as an example, through corresponding needlescopic instrument access port (42) of the rack (28) once direct visualization using a laparoscope (62) confirms that a secure attachment of laparoscopic head (32) to the threaded end (22) of needlescopic instrument (10) has been accomplished. The engagement of the needlescopic instrument threaded end (22) and any one of the instrument heads (30, 32, 34, and 36) may require two separate connections. The threaded end (22) would provide the male portion of the connection and the desired head would receive the threaded end (22) as the female portion of the connection.

Figure 5:
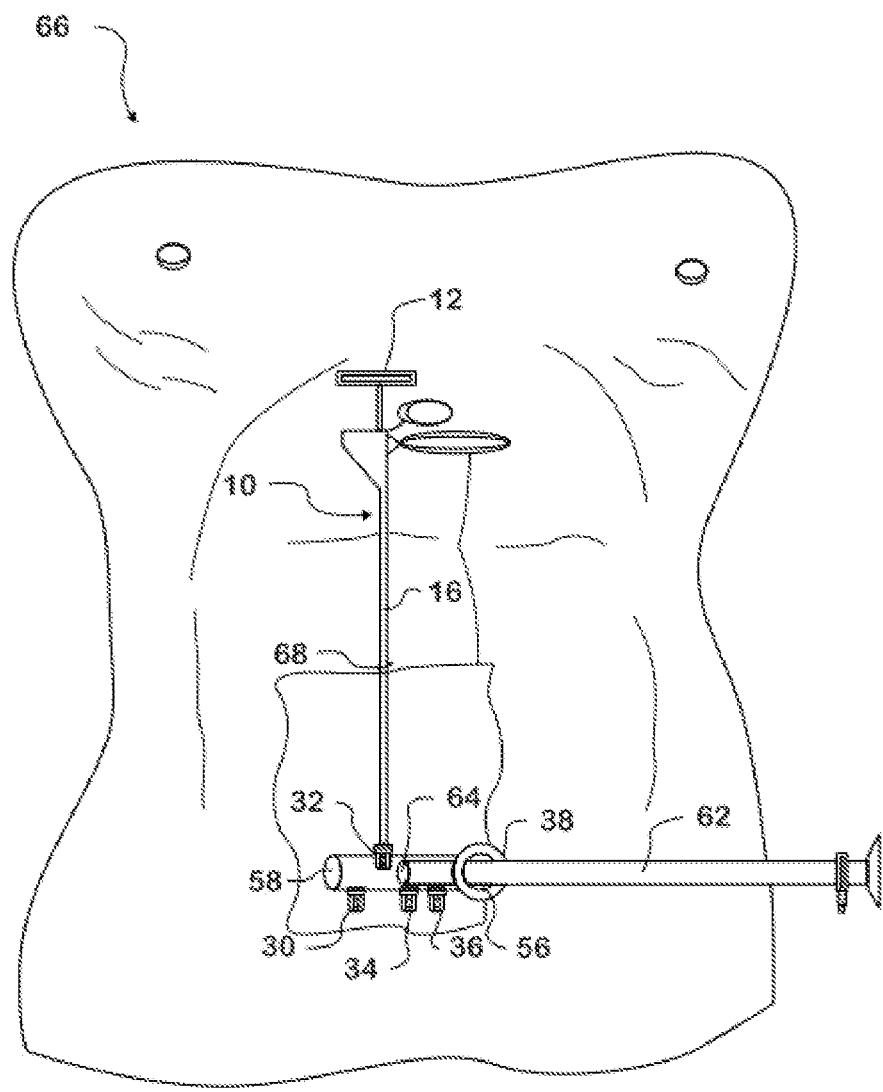
FIG. 5 provides a perspective view of the system as employed in the abdominal cavity of a patient, as an example.

Turning now to FIG. 5, an abdomen (66) is shown wherein a needlescopic procedure is being performed. The needlescopic instrument (10) is inserted into the abdomen (66) via a tiny incision (68) and the threaded end (22) (not shown) is extended. The trocar/cannula device (38) is inserted into the abdomen (66) via another suitably sized incision (not shown). The threaded end (22) engages an instrument head (i.e. 32) under direct visualization through the distal lens (64) of the laparoscope (62) and the instrument head (i.e. 32) is then extracted from the rack (28) (FIG. 4) into the abdomen (66) for use without any further incisions, trocar/cannula devices, or laparoscope devices being needed.

Figure 6A:
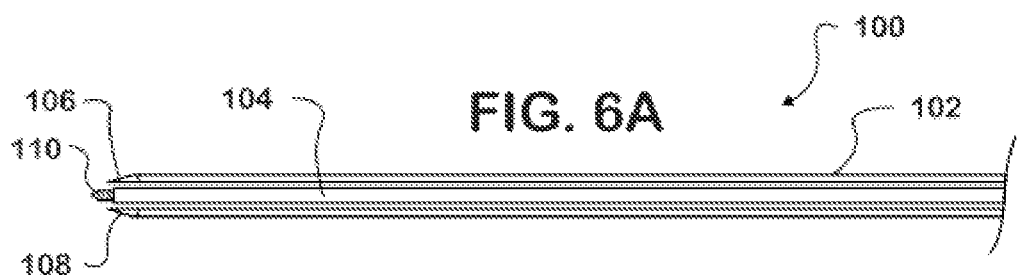
FIG. 6A provides a longitudinal sectional view of a distal portion of a further embodiment of a needlescopic instrument.

Turning now to FIG. 6A, it provides a sectional view of the further embodiment (100) of needlescopic instrument (10) having a hollow shaft (102) housing a sliding rod (104). A tapered distal end (106) of the hollow shaft (102) houses distal end (108) of the sliding rod (104) incorporating a tapered threaded tip (110). The tapered threaded tip (110) is sized and configured to engage a laparoscopic head (not shown) as well.

Figure 6B:
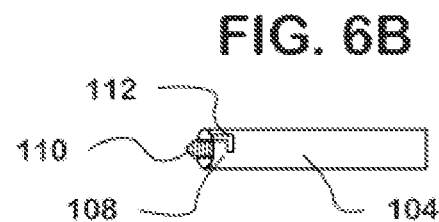
FIG. 6B provides an enlarged view of the distal tip of a threaded rod of the needlescopic instrument of FIG. 6A showing a secondary locking slot for engagement to an instrument head which may accommodate same.

Turning now to FIG. 6B, a latch locking mechanism (112) may be provided for engaging the tapered threaded tip (110) to the laparoscopic head (not shown). The needlescopic instrument (100) is not limited to this type of configuration. Various engagement methods would be useful as understood by those skilled in the art. The tapered distal end (106) may also be magnetized and use magnetic forces to guide the tapered threaded tip (110) into engagement with a head (not shown).

Figure 7A:
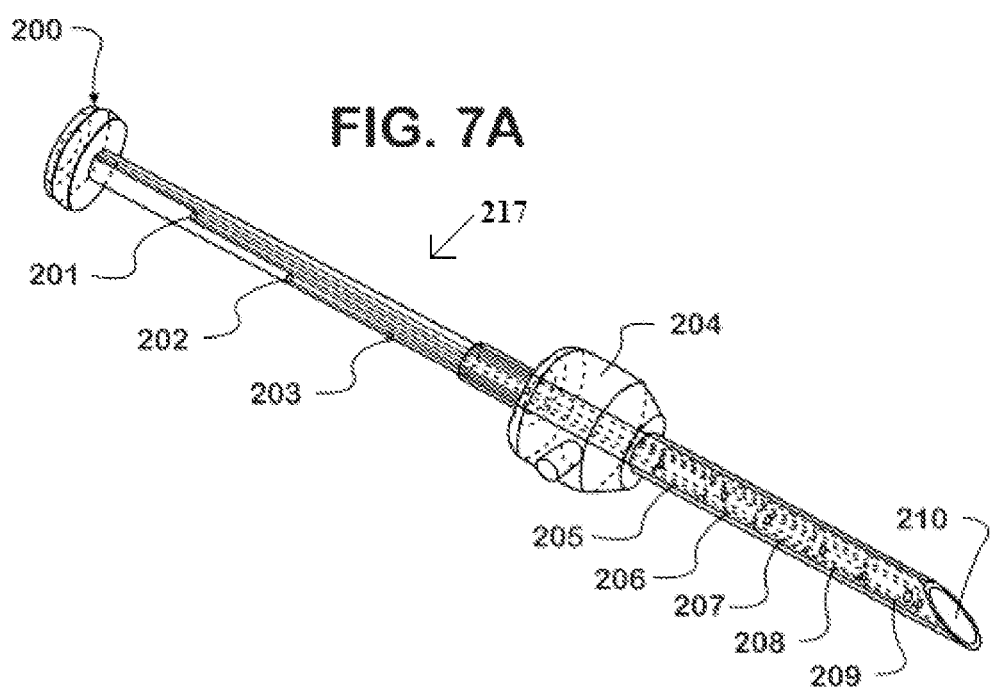
FIG. 7A provides a perspective view of an alternative embodiment of the system including a radial firing assembly.

With respect to FIG. 7A a radial firing assembly (217) is shown having staggered pushrods (201, 202, 203), controlled by the push rod handle (200), used in extending the generically embodied heads (205, 206, 207, 208, 209) through a distal opening (220) of the trocar (238). The pushrods may be constructed of plastics or other industry standard materials.

Figure 7B:
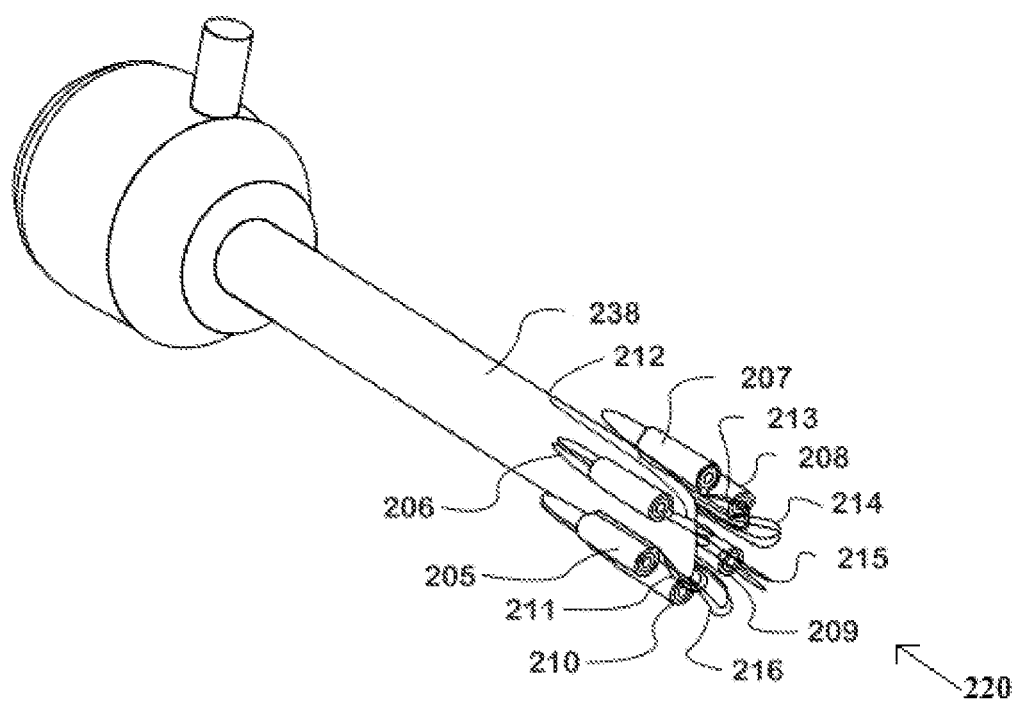
FIG. 7B provides a perspective view of an alternative embodiment of a radial firing assembly.

With respect to FIG. 7B a plurality of generically embodied laparoscopic heads (205, 206, 207, 208, 209, 210) are shown in the positions they are configured to take after exiting the distal trocar/cannula opening (220) through use of flexible metallic connectors or wires (211, 212, 213, 214, 215, 216) constructed of a memory material used to position the instrument head into desired orientation about the distal end of the trocar/cannula (238).

Figure 7C:
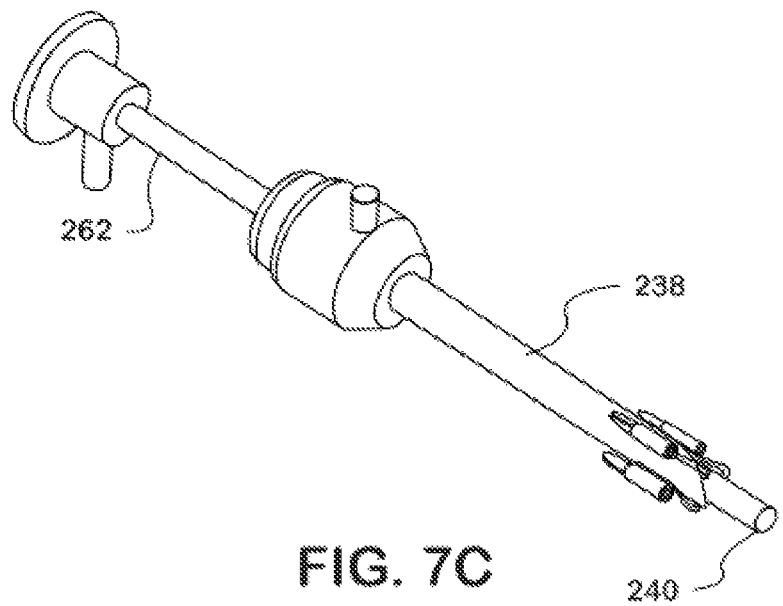
FIG. 7C provides a perspective view of a deployed radial firing assembly with laparoscope fully inserted therethrough.

With respect to FIG. 7C a fully deployed distal end (240) of a laparoscope (262) passes thru the trocar cannula (238), showing that the laparoscope (262) may pass freely thru the trocar/cannula (238) once the various laparoscopic heads are fully deployed.

Figure 8:
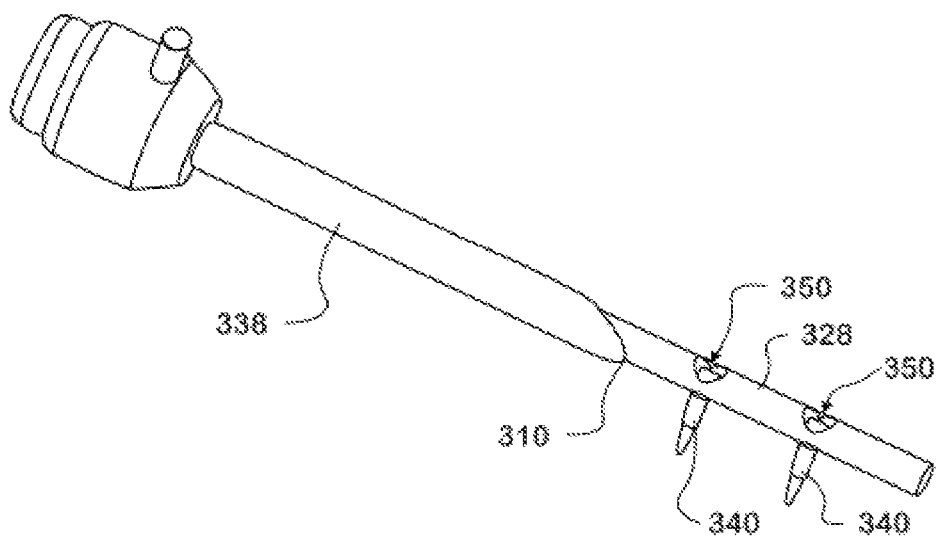
FIG. 8 provides a perspective view of another embodiment of a head rack fully deployed extending beyond the distal end of a trocar.

With respect to FIG. 8 a trocar/cannula (338) is presented having a further embodiment of a head rack (328) extending past the distal end (310) of the trocar/cannula (338). One or more head(s) (340) is housed completely within the rack (328) while passing through the trocar/cannula (338) and then become fully extended through any suitable means, such as spring biasing and at least one access opening (350) is provided for allowing engagement of the head to a needlescopic instrument (not shown).

Figure 9:
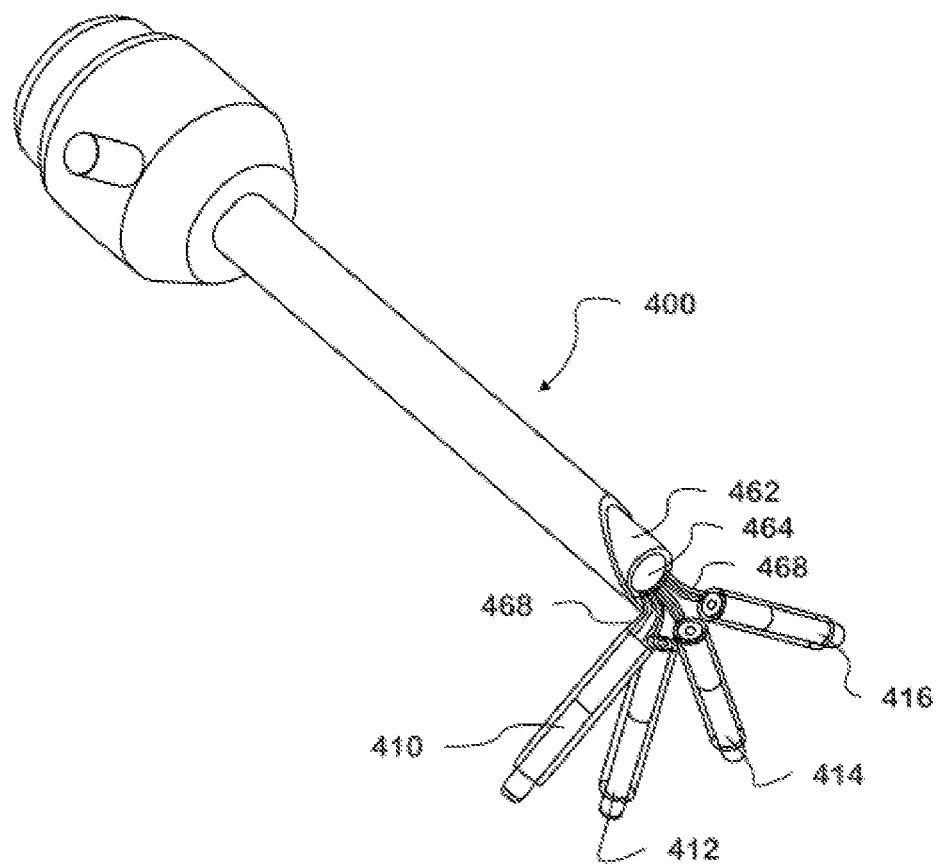
FIG. 9 provides a perspective view of a radial deployment of instrument heads with a laparoscope viewing the attachment heads.

With respect to FIG. 9, showing a further exemplary embodiment of a head deployment configuration, a trocar/cannula (400) is presented having a laparoscope (462) having full view of a plurality of deployed heads (410, 412, 414, and 416) extending outwardly of the trocar/cannula (400). Laparoscope lens (464) allows for direct visualization for attachment of the needlescopic instrument (not shown) to the heads (410, 412, 414, and 416). In this configuration thin attachment members (468) are used to hold the heads (410, 412, 414, and 416) in place, while allowing the laparoscope to pass through the trocar/cannula (400) unhindered. The thin attachment members (468) may be made of various flexible industry standard materials.

As will be recognized by those of ordinary skill in the pertinent art, numerous modifications and substitutions can be made to the above-described embodiments of the present invention without departing from the scope of the invention. Accordingly, the preceding portion of this specification is to be taken in an illustrative, as opposed to a limiting, sense.

The invention claimed is:

1. A system for creating a functional engagement between a needlescopic instrument and a laparoscopic head, said system comprising:
   a needlescopic instrument;
   a carrier defining a lumen, and having a proximal end and a distal end;
   at least one laparoscopic head receivable within said lumen of said carrier; and
   an actuator configured to move said at least one laparoscopic head from a first position wherein said at least one laparoscopic head is substantially entirely positioned within said lumen, to a second position wherein a substantial entirety of said at least one laparoscopic head is positioned outside of said lumen while still being retained by said carrier;
   wherein in said second position, said lumen is substantially unobstructed, permitting insertion of a laparoscope into said lumen from said proximal end of said carrier such that said laparoscope is permitted to pass through said lumen from said proximal end to said distal end substantially unobstructed, such that a proximal end of said at least one laparoscopic head can be coupled to said needlescopic instrument under direct visualization using said laparoscope.

2. The system of claim 1 wherein engagement between said needlescopic instrument and said at least one laparoscopic head is accomplished through screwing or clicking the at least one laparoscopic head onto a mating distal end of the needlescopic instrument, the mating distal end being screw threaded or incorporating a physical feature shaped to lock into laparoscopic head.

3. The system of claim 2 wherein there is further provided a locking mechanism for locking the laparoscopic head to the needlescopic instrument.

4. The system of claim 1 wherein:
   the carrier includes a first opening and a cooperating second opening aligned with the first opening;
   wherein the first opening is positioned such that the actuator may pivot the at least one laparoscopic head into the first opening such that said proximal end of said at least one laparoscopic head faces said second opening, and
   wherein the second opening is positioned so as to receive a distal end of the needlescopic instrument therethrough for attachment to said at least one laparoscopic head.

5. The system of claim 4 wherein the second opening comprises an elongate slit.

6. The system of claim 1 wherein said carrier is sized and configured to allow insertion thereof through a trocar/cannula into a body cavity.

7. The system of claim 1 wherein said actuator is one of a push rod or said laparoscope, said push rod or laparoscope being configured to physically contact the at least one laparoscopic head to move the at least one laparoscopic head to the second position.

8. A system for creating a functional engagement between a needlescopic instrument and a selected one of a plurality of laparoscopic heads, comprising:
   a needlescopic instrument;

a plurality of laparoscopic heads disposed in a carrier;

wherein each of the plurality of laparoscopic heads is movable from a first position in which said laparoscopic head is substantially entirely positioned within said carrier, to a second position in which a substantial entirety of said laparoscopic head is positioned outside of said carrier while still being retained by said carrier;

wherein in said second position, an interior passageway of said carrier is substantially unobstructed, permitting insertion of a laparoscope into said carrier from a proximal end of said carrier such that said laparoscope is permitted to pass through said carrier from said proximal end to a distal end of said carrier substantially unobstructed, such that a proximal end of said at least one laparoscopic head can be coupled to said needlescopic instrument under direct visualization using said laparoscope.

9. The system of claim 8 wherein the carrier includes a plurality of first openings and a plurality of cooperating second openings aligned with the first openings;

wherein the first openings are positioned such that the plurality of laparoscopic heads may each pivot into a respective one of the first openings such that said proximal end of each laparoscopic head faces a respective second opening; and wherein said second openings are positioned so as to receive a distal end of said needlescopic instrument therethrough for attachment to a laparoscopic head of said plurality of laparoscopic heads positioned in a corresponding first opening of the plurality of first openings.

10. The system of claim 9 wherein the second opening comprises an elongate slit.

11. The system of claim 9 wherein the laparoscopic heads may be pivoted into position with a push rod or a distal end of the laparoscope.

12. The system of claim 8 wherein the wherein engagement is accomplished through screwing a selected laparoscope head onto a mating distal end of the needlescopic instrument, the distal end being a screw threaded end.

13. The system of claim 12 wherein there is further provided a locking mechanism for locking the selected laparoscopic head to the needlescopic instrument.

14. The system of claim 8 wherein said carrier is sized and configured to allow insertion thereof through a trocar/cannula into a body cavity.

15. The system of claim 8 wherein the laparoscopic heads are interchangeable and are disconnected from the needlescopic instrument in a manner opposite to their connection thereto and then the needlescopic instrument is connected to another desired one of the plurality of laparoscopic heads under direct visualization using the laparoscope, with the disconnected head being repositioned for potential later reuse.

16. The system of claim 8 wherein the number of laparoscopic heads required for a particular operation are contained within the carrier.

* * * * *